(12) United States Patent
Yogesan et al.

(10) Patent No.: US 8,118,428 B2
(45) Date of Patent: Feb. 21, 2012

(54) OPTHALMIC CAMERA AND OPTHALMIC CAMERA ADAPTOR

(75) Inventors: Kanagasingam Yogesan, Nedlands (AU); Gabriel Suplewski, Iluka (AU); Matthew David Spark, High Wycombe (AU); Ian Jeffrey Constable, Nedlands (AU)

(73) Assignee: The Lions Eye Institute Ltd., Nedlands (AU)

( * ) Notice: Subject to any disclaimer, the term of this patent is extended or adjusted under 35 U.S.C. 154(b) by 292 days.

(21) Appl. No.: 11/612,464

(22) Filed: Dec. 18, 2006

(65) Prior Publication Data
US 2008/0030679 A1 Feb. 7, 2008

Related U.S. Application Data

(63) Continuation of application No. PCT/AU2005/00880, filed on Jun. 20, 2005.

(30) Foreign Application Priority Data

Jun. 18, 2004 (AU) ................................ 2004903312

(51) Int. Cl.
*A61B 3/10* (2006.01)
(52) U.S. Cl. ........................................ 351/205; 351/206
(58) Field of Classification Search .................. 351/205, 351/206
See application file for complete search history.

(56) References Cited

U.S. PATENT DOCUMENTS

| | | | |
|---|---|---|---|
| 5,181,345 A * | 1/1993 | Kulan | 451/11 |
| 5,285,223 A | 2/1994 | Ueno et al. | |
| 5,880,813 A | 3/1999 | Thall | |
| 6,637,882 B1 | 10/2003 | Goldfain et al. | |
| 2002/0025145 A1 * | 2/2002 | Nanjyo | 396/18 |
| 2003/0011757 A1 | 1/2003 | Hirohara et al. | |
| 2004/0021858 A1 * | 2/2004 | Shima et al. | 356/241.1 |
| 2005/0008774 A1 * | 1/2005 | Borgharkar et al. | 427/162 |
| 2006/0038881 A1 * | 2/2006 | Starkweather et al. | 348/51 |

FOREIGN PATENT DOCUMENTS

| | | |
|---|---|---|
| GB | 2 077 946 | 12/1981 |
| GB | 2 182 164 | 5/1987 |
| JP | 08-010228 | 1/1996 |
| JP | 9-266888 | 10/1997 |
| JP | 10-118030 | 5/1998 |
| JP | 2002-051985 | 2/2002 |
| WO | WO 2004/112599 | 12/2004 |

* cited by examiner

*Primary Examiner* — Ricky Mack
*Assistant Examiner* — James Jones
(74) *Attorney, Agent, or Firm* — Vedder Price P.C.; Thomas J. Kowalski; Deborah L. Lu

(57) ABSTRACT

An ophthalmic camera (10) comprising a camera (12) having a lens (18) aligned with a second lens (16) and at least one illumination means (14). The illumination means (14) is capable of movement relative to the camera lens (18) so that the beam of light emitted by the illumination means (14) is able to be focused by the second lens (16) through the pupil onto the fundus. In another embodiment, the ophthalmic camera comprises a camera (52), an illumination means (54) and a beamsplitter (58). The camera (52) and the beamsplitter (58) from an alignment axis X and the illumination means (54) together with the beam splitter (58) form an illumination axis Y perpendicular to the alignment axis X. The illumination means (54) is capable of movement relative to the illumination axis Y so that the beam of light reflected by the beamsplitter (58) towards the pupil (70) is substantially the same size as the pupil (70) to maximize the amount of light entering the pupil without impinging upon the iris to avoid contracting of the pupil (70).

29 Claims, 3 Drawing Sheets

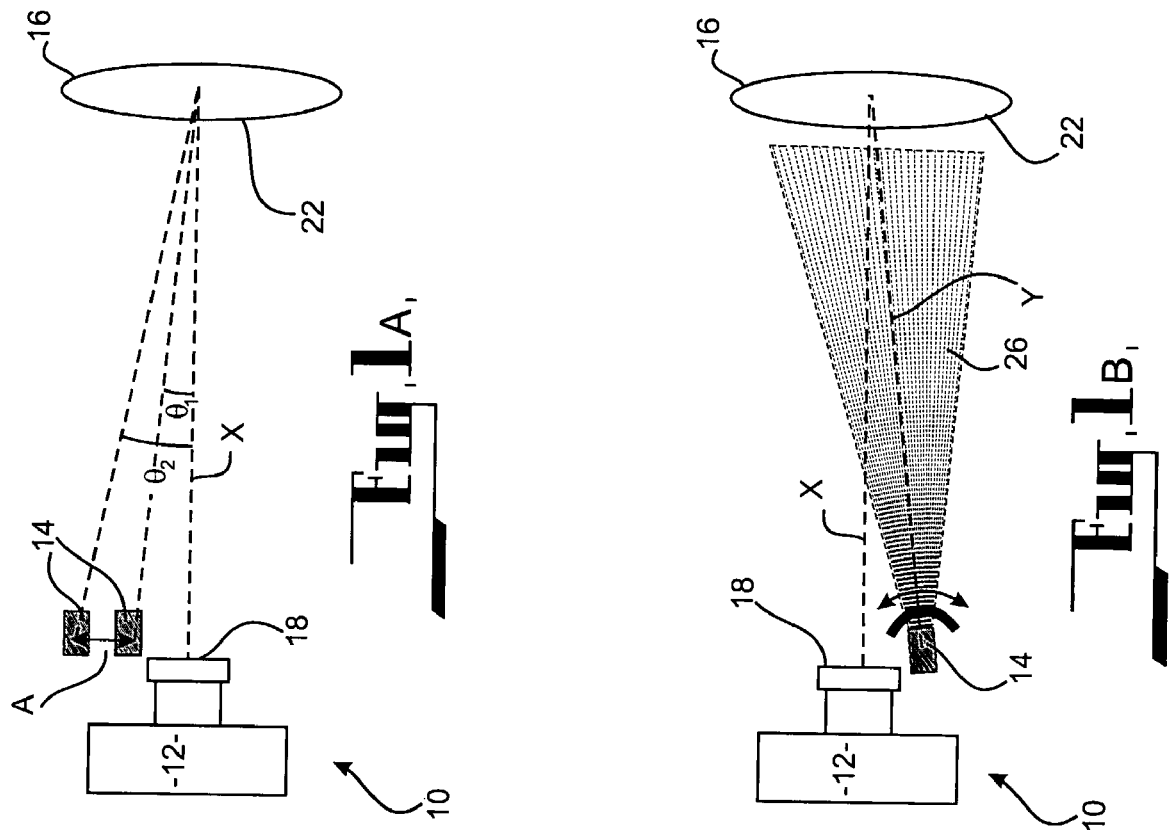
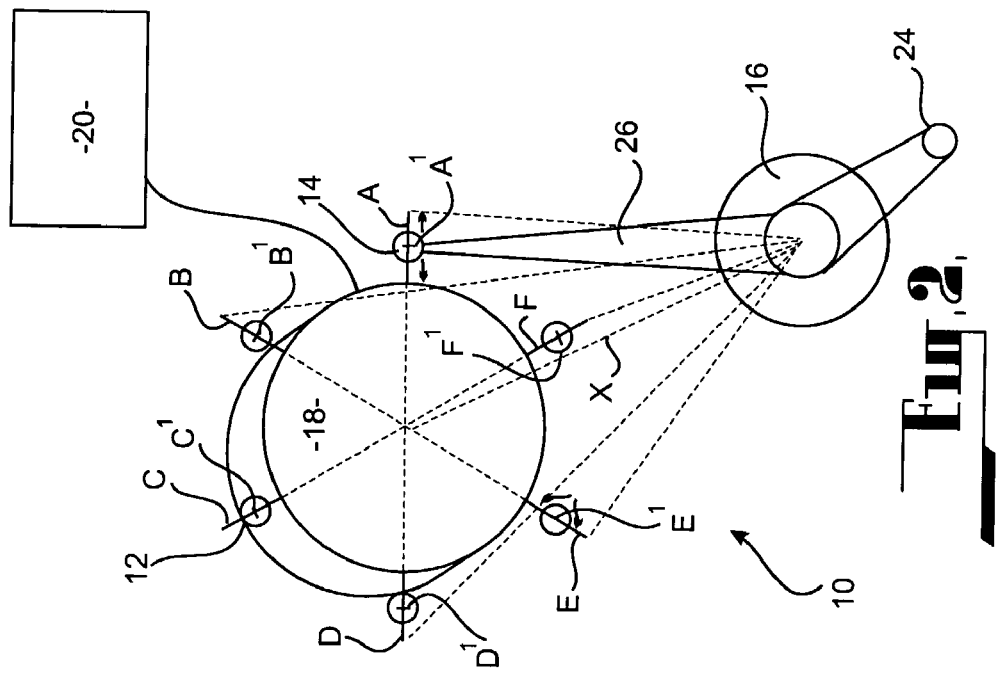

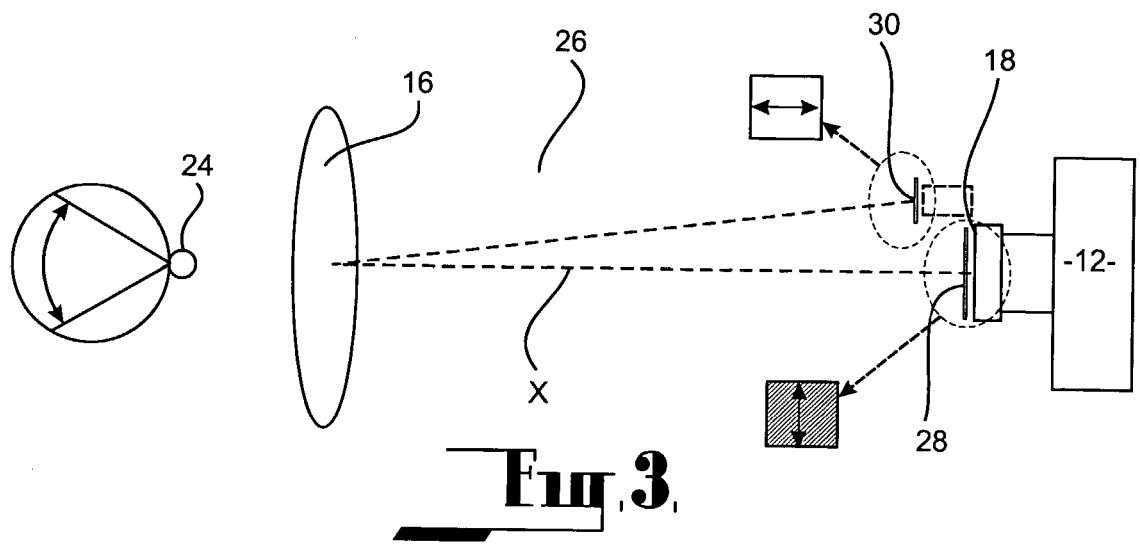
Fig. 3
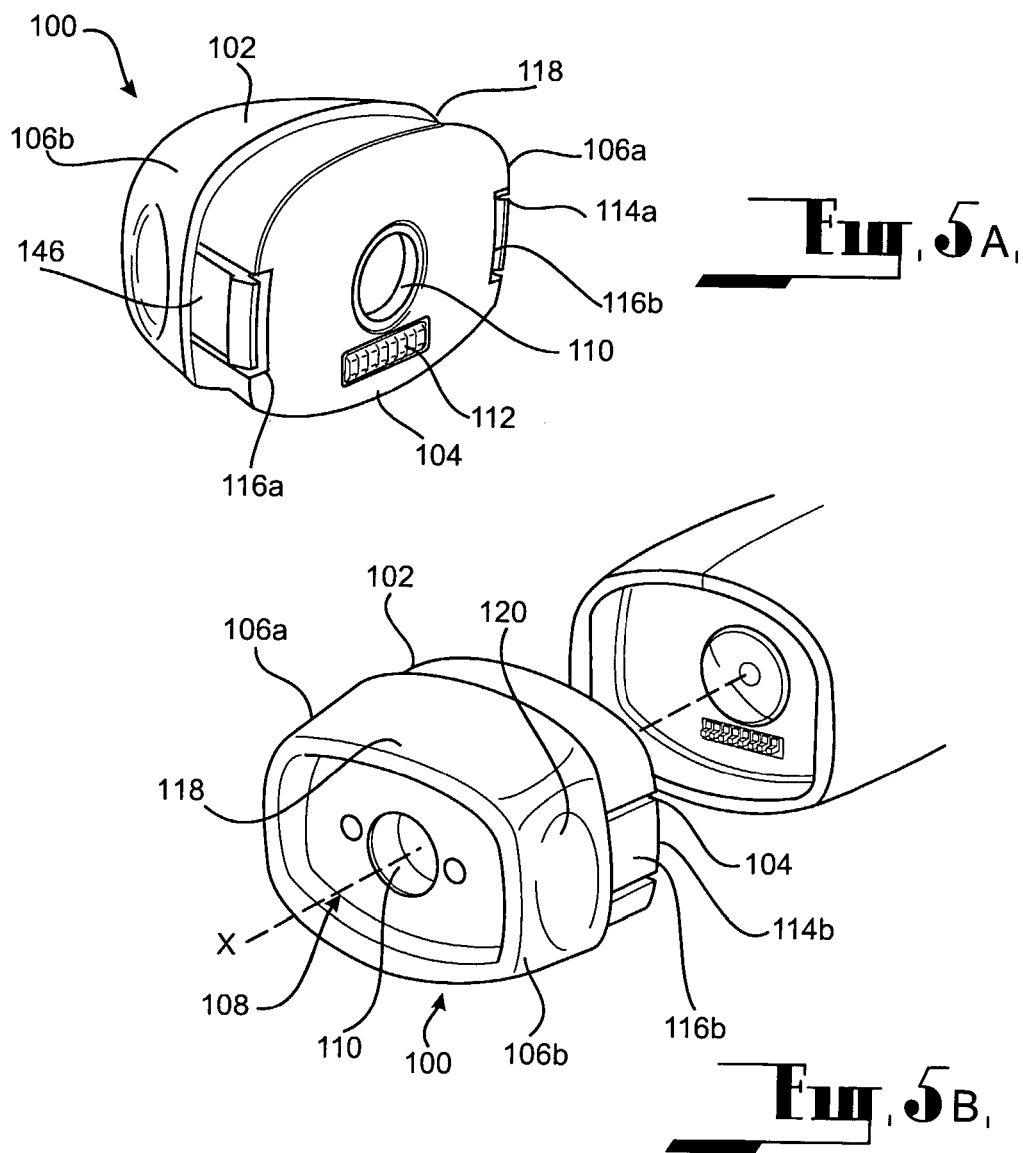
Fig. 5A
Fig. 5B

OPTHALMIC CAMERA AND OPTHALMIC CAMERA ADAPTOR

CROSS REFERENCE TO RELATED APPLICATIONS

This application is a continuation-in-part of International Application No. PCT/AU2005/000880, filed Jun. 20, 2005, published as WO 2005/122874 on Dec. 29, 2005, and claiming priority to Australian Application No. 2004903312, filed Jun. 18, 2004.

The foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to an ophthalmic camera and an ophthalmic camera adaptor. In particular, the invention relates to the optical arrangement that forms the basis for the ophthalmic camera and ophthalmic camera adaptor.

Throughout the specification, unless the context requires otherwise, the word "comprise" or variations such as "comprises" or "comprising", will be understood to imply the inclusion of a stated integer or group of integers but not the exclusion of any other integer or group of integers.

BACKGROUND ART

The following discussion of the background to the invention is intended to facilitate an understanding of the present invention. However, it should be appreciated that the discussion is not an acknowledgement or admission that any of the material referred to was published, known or part of the common general knowledge of a skilled person in any jurisdiction as at the priority date of the application.

Images of the fundus of a patient's eye can degrade due to many factors. Such factors include:
  reflection of light from the cornea or iris;
  reflection of light from the walls of the ophthalmic lens; and
  use of an incorrect level of illumination for the pupil colour of the patient's eye.

One method of overcoming some of the above problems is to use low level illumination devices. However, using such illumination devices, typically, reduces the field of view of the image and may not be appropriate for the fundus being examined.

It is therefore an object of the present invention to provide an optical arrangement that reduces the level of reflection by one or more of the cornea, iris, or walls of the ophthalmic lens.

DISCLOSURE OF THE INVENTION

Broadly, the invention lies in a camera having a lens, at least one illumination means; and a second lens; wherein and the centres of the second lens and camera lens are aligned to form an alignment axis and wherein said one illumination means is capable of linear movement along a radial axis of the camera lens and pivotal movement about a pivot point thereof, such that the circle of light emitted said one illumination means can be adjusted towards or away the alignment axis to remain focused relative to the centre of the second lens.

Preferably, the second lens is an ophthalmic lens and the second lens is equal to or smaller than the camera lens.

The illumination angle of the at least one illumination means may be adjustable. This may be an inherent characteristic of the at least one illumination means or achieved by an external element, such as a collimator. In this manner, the circle of light emitted by the at least one illumination means, at the point of intersection with the ophthalmic lens, is of a size that, when the light is focused by the ophthalmic lens onto a fundus, the angle of the focused light provides a wide field of view for the size of the fundus being examined.

The field of view of the camera lens may also be adjustable. Ideally, the field of view of the camera lens is restricted to the same size as the size of the fundus being examined. This may be achieved by means of an iris.

The at least one illumination means may surround the circumference of the camera lens. Each illumination means is preferably equidistant from its adjacent illumination means to provide a homogenous light source. Preferably, the illumination means are solid state LEDs, however, light bulbs with appropriate focusing means may also be used.

The at least one illumination means may also be of variable intensity. In this manner, the at least one illumination means can adjust the level of illumination provided by the emitted circle of light to more appropriately accord with the colour of the fundus being examined. The level of intensity may be a function of a setting of the ophthalmic camera.

The camera preferably has a high sensitivity to low light. Ideally, the camera has a sensitivity level of <0.05 lux and/or a lens of 5 to 8 mm in diameter.

The ophthalmic lens is preferably in the range of 20 to 90 dioptres, with 40 being considered optimal. The ophthalmic lens may have an anti-reflective coating.

The ophthalmic lens may be capable of linear movement along the alignment axis to allow for focusing. Alternatively, other means of focusing the ophthalmic camera may be employed.

Ideally, the ophthalmic camera can be set to one or more settings. Each setting represents a pupil size. When a setting is changed, the at least one illumination means moves linearly along its radial axis to the position specified by the new setting and pivots about the radial plane until the circle of light emitted by the at least one illumination means is focused on the centre of the ophthalmic lens. Alternatively, the settings may be omitted and control of the linear and pivotal movement of the at least one illumination means may be by means of one or more manual controls. Both the setting control and the manual control may be expanded to further control the illumination angle of the at least one illumination means and/or the field of view of the camera lens.

Control of one or more of the linear and pivotal movement of the at least one illumination means, the illumination angle of the at least one illumination means and the field of view of the camera lens, may be controlled automatically by a control means in response to the estimated size of the fundus to be examined as determined by an automated measuring means.

The ophthalmic camera may also include magnification lenses. Each magnification lens may be associated with one or more settings, such that on choosing a setting, its associated magnification lenses are positioned within the optical axis of the camera and in-between the ophthalmic lens and the camera lens.

The camera may be colour or monochromatic, digital or analogue, as required.

Filters may be positioned in front of the camera lens and the at least one illumination means, the filters being of opposite polarisation to each other.

The invention may also be disclosed in an ophthalmic camera adaptor incorporating the optics of any of the previous embodiments. The ophthalmic camera adaptor omits the camera.

The invention may also be disclosed in a method of imaging the fundus of the eye.

In accordance with a first aspect of the invention there is provided an ophthalmic camera for taking an image of the fundus of an eye, comprising a camera having a camera lens; at least one illumination means; and a second lens, the centres of the second lens and camera lens being aligned to form an alignment axis and the illumination means being movable relative to the alignment axis and the second lens, so that the beam of light emitted by the illumination means is able to be focused by the second lens through the pupil onto the fundus.

According to a preferred feature of the invention, the illumination means comprises a plurality of illumination devices, the illumination devices disposed to surround the circumference of the camera lens and be spaced equidistant from adjacent illumination devices.

According to a preferred feature of the invention, the ophthalmic camera further comprises control means, the control means having a plurality of settings such that, when the setting of the control means is changed, said illumination means moves linearly along its radial axis to the position specified by the new setting and pivots about the axial plane until the circle of light emitted by said one illumination means is focused relative to the centre of the second lens.

According to a preferred feature of the invention, the ophthalmic camera includes automated measuring means, the automated measuring means operable to analyse a fundus being examined and change the setting of the control means to the most appropriate setting on the basis of the analysis of the pupil.

According to a preferred feature of the invention, the ophthalmic camera includes a first polariser located within the alignment axis and positioned in front of the second lens and a second polariser attached to each illumination means such that light emitted by the illumination means passes through the second polariser, the first polariser being oppositely polarised to the second filter to thereby filter the light.

According to a second aspect, the invention resides in an ophthalmic camera comprising a camera having a camera lens; an illumination means; a second lens; a beam splitter; and a light focusing lens; the centres of the second lens, the camera lens and the beam splitter being aligned to form an alignment axis, and the centres of the beam splitter, light focusing lens and the illumination means being aligned to form an illumination axis perpendicular to the alignment axis, the illumination means being movable relative to the illumination axis and the light focusing lens so that the beam of light from the illumination means is focused by the light focusing lens towards the beam splitter, and reflected by the beam splitter along the alignment axis towards and through the pupil, the illumination means thereby being movable relative to the alignment axis and the second lens, wherein the position of the illumination means is adjustable to focus the beam of reflected light so that it is substantially the same size as the pupil to maximise the amount of light entering the pupil without impinging upon the iris to thereby avoid contraction of the pupil.

According to a preferred embodiment, the beam splitter is a 50/50 beam splitter.

According to a preferred feature of the invention, the illumination means is able to move linearly along the illumination axis such that the light reflected by the beam splitter towards the retina is substantially aligned with the centre of a first surface of the second lens.

According to a preferred embodiment, the illumination means is able to pivot about a pivot point to permit the illumination axis to be moved and adjusted relative to said alignment axis.

According to a preferred embodiment, the ophthalmic camera includes control means, the control means having a plurality of settings such that, when the setting of the control means is changed, said one illumination means moves linearly along the illumination axis to a predetermined position associated with the new setting.

According to a preferred feature of the invention, the ophthalmic camera includes automated measuring means, the automated measuring means operable to analyse the retina being examined and change the setting of the control means to the most appropriate setting on the basis of the analysis of the pupil.

According to a preferred embodiment, the second lens is an ophthalmic lens.

According to a preferred embodiment, the camera has a high sensitivity to low light.

According to a preferred embodiment, the second lens is in the range of 20 to 90 dioptres.

According to a preferred embodiment, the second lens is substantially 40 dioptres.

According to a preferred embodiment, the ophthalmic camera includes focussing means for focusing the second lens.

According to a preferred embodiment, the focusing means is means for allowing linear movement of the second lens along the alignment axis.

According to a preferred feature of the invention, the illumination angle of the illumination means is adjustable.

According to a preferred embodiment, the ophthalmic camera includes at least one collimator, each collimator associated with an illumination means operable to adjust the illumination angle of the associated illumination means.

According to a preferred embodiment, the field of view of the camera lens is adjustable.

According to a preferred feature of the invention, the ophthalmic camera includes an iris, the iris operable to adjust the field of view of the camera lens.

According to a preferred embodiment, the intensity of the light generated by the illumination means is adjustable.

According to a preferred embodiment, the illumination means is a solid state light emitting diode.

According to a preferred embodiment, the illumination means is a light bulb with associated appropriate focusing means.

According to a preferred embodiment, at least one surface of at least one lens has an anti-reflective coating.

According to a third aspect, the invention resides in an adaptor for an ophthalmic camera having a body and a camera housed within the body, the adaptor comprising:
  optics for illuminating a subject within the optical axis of
    the camera as described above;
  means for releasably engaging the body; and
  an aperture extending therethrough;

wherein, when releasably engaged with the body, the aperture aligns with the optical axis such that least a portion of the optical axis of the camera is not obscured.

According to a fourth aspect, the invention resides in a method of imaging a fundus comprising the steps of:

moving an illumination means along a radial axis of a camera lens; and pivoting the illumination means such that the circle of light emitted by the illumination means can be focused relative to the centre of a second lens;

wherein the centre of the second lens is in alignment with the centre of the camera lens.

According to a preferred feature of the invention, the method includes the further step of:

moving the illumination means along the radial axis to a predetermined position associated with a setting of a control means when the control means is set to the associated setting.

According to a preferred feature of the invention, the method includes the steps of:

analysing the pupil being examined;

determining the most appropriate associated setting on the basis of the analysis of the pupil; and changing the setting of the control means to the most appropriate associated setting.

According to a preferred feature of the invention, the method includes the steps of:

directing the circle of light through a first polariser; and taking an image of the circle of light through a second polariser of opposite polarisation to the first polariser.

According to a fifth aspect the invention resides in a method of imaging a fundus comprising:

directing light emitted by an illumination means to a light focusing lens; and focusing the light towards a beam splitter to be reflected by the beam splitter towards the fundus so that the size of beam of light can be of commensurate to the size of the pupil;

wherein the centres of the beam splitter, light focusing lens and illumination means are aligned to form an illumination axis and the centres of a camera lens, second lens and the beam splitter are aligned to form an alignment axis perpendicular to the illumination axis.

According to a preferred feature of the invention, the method includes the step of moving the illumination means linearly along the illumination axis such that the centre of the circle of light reflected by the beam splitter towards the pupil is substantially aligned relative to the centre of a first surface of the second lens.

According to a preferred feature of the invention, the method includes the step of pivoting the illumination means about the place that includes the optical axis and the illumination axis.

According to a preferred feature of the invention, the method includes the further step of:

moving the illumination means along the radial axis to a predetermined position associated with a setting of a control means when the control means is set to the associated setting.

According to a preferred feature of the invention, the method includes the steps of:

analysing the pupil being examined;

determining the most appropriate associated setting on the basis of the analysis of the pupil; and changing the setting of the control means to the most appropriate associated setting.

According to a preferred feature of the invention, the method includes further comprising the step of focussing the second lens:

According to a preferred feature of the invention, the method includes the step of linearly moving the second lens along the alignment axis to focus the second lens.

According to a preferred feature of the invention, the method includes the step of adjusting the illumination angle of the illumination means.

According to a preferred feature of the invention, the method includes including the step of adjusting the field of view of the camera lens.

According to a preferred feature of the invention, the method includes the step of adjusting the intensity of the light generated by the illumination means.

The invention will now be more fully understood in light of the following description of several specific embodiments.

BRIEF DESCRIPTION OF THE DRAWINGS

The invention will now be described, by way of example only, with reference to the accompanying drawings, of which:

FIG. 1a is a schematic of the optics of an ophthalmic camera and ophthalmic camera adaptor of a first embodiment of the present invention showing linear movement of the LED's.

FIG. 1b is a schematic of the optics of the ophthalmic camera and ophthalmic camera adaptor of the first embodiment, similar to FIG. 1b but showing angular movement of the LED's.

FIG. 2 is an isometric view of the schematics of the optics of the ophthalmic camera and ophthalmic camera adaptor of the first embodiment of the present invention.

FIG. 3 is a schematic of the optics of an ophthalmic camera and ophthalmic camera adaptor of a second embodiment of the present invention.

FIGS. 5a and 5b are perspective views of an ophthalmic camera adaptor of the present invention.

BEST MODE(S) FOR CARRYING OUT THE INVENTION

Figure 4:
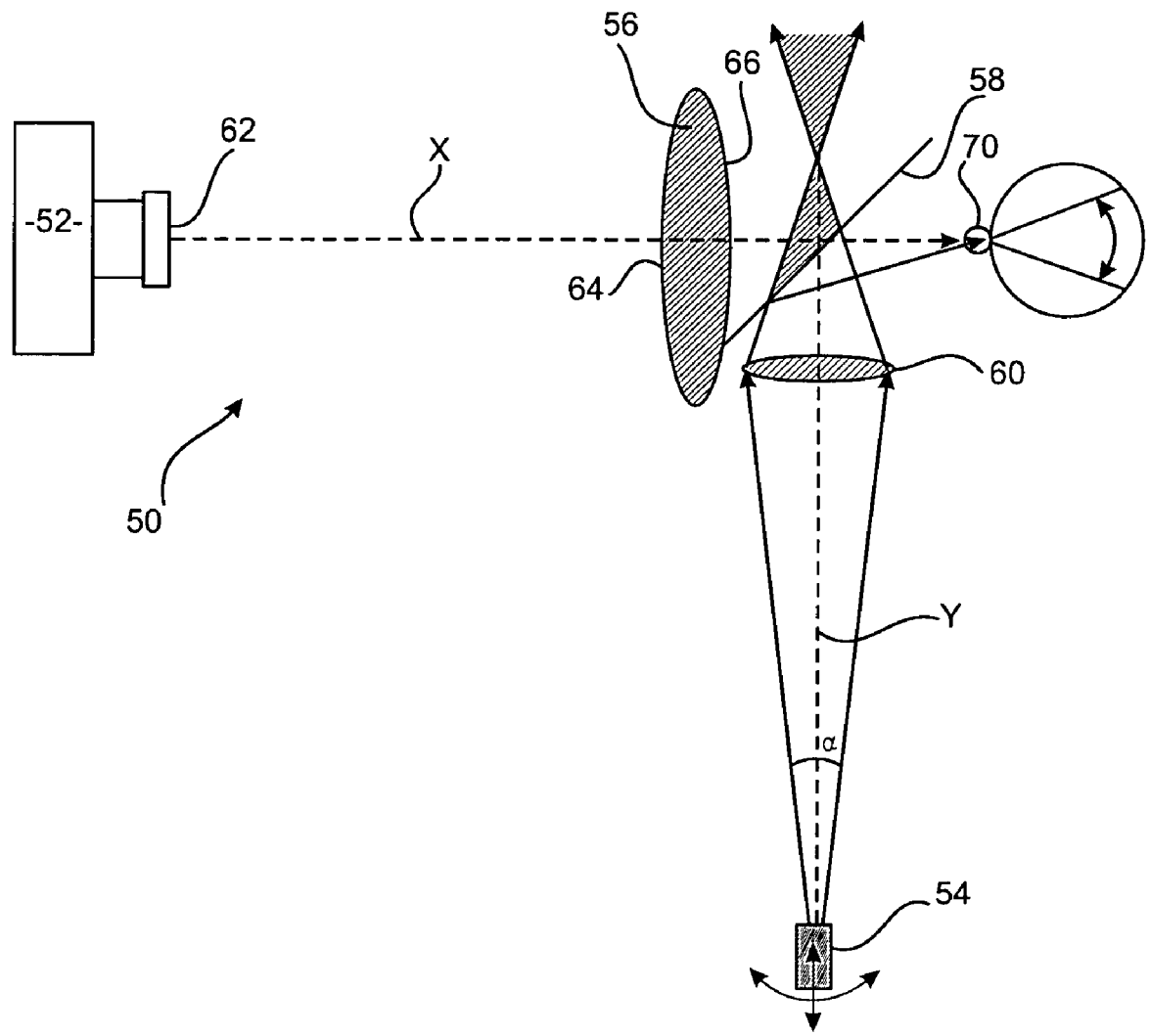
FIG. 4 is a schematic of the optics of an ophthalmic camera and ophthalmic camera adaptor of a third embodiment of the present invention.

The first embodiment of the best mode invention for carrying out the invention is directed towards an ophthalmic camera apparatus 10, generally comprising a camera 12 highly sensitive to low light (ie. somewhere in the range of <0.05 lux), an illumination means in the form of a plurality of solid-state LEDs 14, and an ophthalmic lens 16 all contained within a housing (not shown). This arrangement is shown graphically in FIG. 1.

The camera 12 has a camera lens 18 and so the ophthalmic lens constitutes a second lens of the apparatus 10. Ideally, the camera lens 18 has a diameter of 5-8 mm. The camera lens 18 provides for an adjustable field of view.

The plurality of LEDs 14 surround the circumference of the camera lens 18 and are linked to a control unit 20. The intensity of the light generated by LEDs 14 can be varied by way of the control unit 20.

Each LED 14 is equidistant to its adjacent LEDs 14. Each LED 14 also has an adjustable illumination angle.

As shown in FIGS. 1a and 2, LEDs 14 are able to move linearly along their respective radial axes (marked A through E), relative to the main optical axis X. As shown in FIGS. 1b and 2, each LED 14 is also able to pivot about a pivot point thereof (A' to E'), towards, or away from the camera lens 18, so that the illumination axis Y thereof can move either towards or away the point of intersection of the optical axis X with the ophthalmic lens 16, in order to compensate for linear movement of the LED along its respective radial axis A-E and corresponding displacement of the illumination axis Y relative to the optical axis X.

The ophthalmic lens 16 has an inner convex surface 22 that opposes the camera lens 18. The central axis of the camera lens 18 aligns with the central axis of the inner convex surface 22 to form an alignment axis, which constitutes the main optical axis X. Ideally, the ophthalmic lens 16 is of the same size as, or smaller than, the camera lens 18. An anti-reflective coating may be applied to the ophthalmic lens 16.

The ophthalmic lens is typically in the range of 20 to 90 dioptres, with 40 dioptres considered optimum. To allow for focusing of the ophthalmic lens 16, the ophthalmic lens 16 is capable of linear movement along optical axis X of the monochromatic camera 12.

The position of the LEDs 14, as well as the illumination angle of LEDs 14 and field of view of the camera lens 18, are all a function of the current setting of the ophthalmic camera apparatus 10. Each setting of the ophthalmic camera apparatus 10 represents a range of sizes of a pupil 24 of a patient with being examined with the apparatus. To elaborate, setting 1 is used for pupils of size less than 3 mm;
setting 2 is used for pupils having a size between 3-4 mm; and
setting 3 is used for dilated pupils.
Upon choosing a setting:
The illumination angle of a beam of light 26 generated by each LED 14 along its illumination axis Y is restricted or enlarged, as appropriate, such that the circle generated by the beam of light 26 at the point of intersection with the ophthalmic lens 16 is of a size that, when the light is focused by the ophthalmic lens 16 onto the pupil 24, the angle of the focused light θ provides a wide field of view for the appropriate pupil 24 size.
LEDs 14 move linearly along their respective radial axes (marked A through E) and pivot about their respective pivot point (marked A' through E') such that the centre of the circle generated by the beam of light 26 at the point of intersection with the ophthalmic lens 16 can be precisely adjusted with respect to the centre of the ophthalmic lens 16.
The field of view of camera lens 18 is restricted to substantially the same size as the pupil 24 size associated with the setting.

This allows the same LEDs 14 to be used for pupils 24 of all sizes while negating the need to unnecessarily restrict the field of view of the camera lens 18 to avoid reflection from the cornea or iris. This also means that for larger size pupils 24, the angle of the focused light θ along the illumination axis Y is greater than the angle of the focused light θ generated in respect of smaller size pupils 24.

The second embodiment of the best mode is substantially similar to the first embodiment, where like numerals reference like parts, but involves the use of optical filters. As shown in FIG. 3, a first filter 28 is located along the optical axis X of the camera 12 at a position in front of camera lens 18. A second filter 30 is attached to each LED 14, such that the beam of light 26 emitted thereby passes through the second filter 30.

The first filter 28 is oppositely polarised to second filter 30.

As the beam of light 26 reflects off the fundus 24 it enters the ophthalmic lens 18. On entering the ophthalmic lens 18, the polarisation of the beam of light 26 is reversed. However, as the beam of light 26 enters the ophthalmic lens 18, light that reflects off the two walls of the ophthalmic lens 18 will not be captured by the camera 12 due to the cross-polarisation effect of first and second filters 28, 30.

The third embodiment of the best mode is shown in FIG. 4, and is directed towards an ophthalmic camera apparatus 50 comprising a digital camera 52 highly sensitive to low light (ie. somewhere in the range of <0.05 lux), a solid state LED 54, an ophthalmic lens 56, a beamsplitter 58 and a light focusing lens 60, all contained within a housing (not shown).

The digital camera 52 has a camera lens 62. Ideally, the camera lens 62 has a diameter of 5-8 mm. The camera lens 62 provides for an adjustable field of view.

The ophthalmic lens 56 has an inner convex surface 64 that opposes the camera lens 62. The centre of the camera lens 62 aligns with the centre of the inner surface 64. Ideally, the ophthalmic lens 56 is of the same size as, or smaller than, the camera lens 62.

The ophthalmic lens 56 is typically in the range of 20 to 90 dioptres, with 40 dioptres considered optimum. To allow for focusing of the ophthalmic lens 56, the ophthalmic lens 56 is capable of linear movement along optical axis X of the digital camera 52.

Opposite the outer convex surface 66 of the ophthalmic lens 56, but still within the optical axis X of the digital camera 52, is beamsplitter 58. In this embodiment, beamsplitter 58 is a 50/50 beamsplitter, but beamsplitters of other proportions may be used.

Located substantially at a right angle to the optical axis X of the digital camera 52, as taken at the point of intersection with beamsplitter 58, is illumination axis Y. Located on illumination axis Y are light focusing lens 60 and solid state LED 54. Solid state LED 54 is capable of linear movement along illumination axis Y. Solid state LED 54 is also capable of pivotal movement about a pivot point that permits the illumination axis to be moved and adjusted relative to the optical axis X.

Solid state LED 54 has an adjustable illumination angle. The intensity of the light generated by the solid state LED 54 is also adjustable.

As with previous embodiments of the invention, the position of the solid state LED 54, the illumination angle of LED 54 and the field of view of the camera lens 62, are all a function of the current setting of the ophthalmic camera apparatus 50. Each setting of the ophthalmic camera 50 apparatus represents a range of sizes for the pupil 70 of a patient being examined with the apparatus. To elaborate, setting 1 is used for pupils 70 of size less than 3 mm;
setting 2 is used for pupils 70 having a size between 3-4 mm; and
setting 3 is used for dilated pupils 70.
Upon choosing a setting:
The illumination angle of light emitted by solid state LED 54 is restricted or enlarged, as appropriate, such that the circle of light reflected by the beamsplitter 58 towards pupil 70 is of a size that the angle of the focused light θ provides a wide field of view for the appropriate pupil 24 size.
Solid state LED 54 moves linearly along illumination axis Y and pivots about the plane that includes illumination axis Y and optical axis X such that the centre of the circle of light reflected by the beamsplitter 58 towards pupil 70 is substantially aligned with or relative to the centre of the outer surface 66 of the ophthalmic lens 56.
The field of view of camera lens 62 is restricted to substantially the same size as the pupil 70 size associated with the setting.

This also means that for larger size pupils 70, the angle of the focused light θ is greater than the angle of the focused light θ generated in respect of smaller size pupils 70.

The fourth embodiment of the best mode is directed towards an ophthalmic camera adaptor 100. The ophthalmic camera adaptor 100 is shown in FIGS. 5a and 5b.

The ophthalmic camera adaptor 100 consists of a body 102. In the embodiment being described, body 102 is substantially rectangular in shape and has a rear face 104, two sides 106a, 106b and a front face 108.

Located centrally about rear face 104 is an aperture 110. Aperture 110 extends through the ophthalmic adaptor 100 such that the aperture 110 is also located centrally about front face 108. Situated adjacent aperture 110 is an interface contact 112.

Adjacent face 104 are two snap clips 114a, 114b. Snap clip 114a extends from side 106a, while snap clip 114b extends from side 106b. Each snap clip 114 has an internal recess 116a, 116b positioned such that, when appropriate pressure is applied, the snap clips 114 can flex towards aperture 110. Snap clips 114a, 114b are adapted to be releasably retained within grooves on the body of a camera (not shown) to which it is ultimately attached.

Surrounding front face 108, and extending along a portion of sides 106 towards rear face 104, is a rubber overmoulding 118. Rubber overmoulding 118 covers a portion 120 of each snap clip 114. Finger grips 122 are formed within the external surface 124 of rubber overmoulding 118 at a position substantially adjacent portion 120.

The optics as described in any of the previous embodiments of the invention can be implemented in this ophthalmic adaptor 100 arrangement. The optics are connected to the interface contact 112 such that control of the optics is facilitated through the interface contact 112.

It should be appreciated by the person skilled in the art that the present invention is not limited to the above embodiments and that variations and modifications thereof are considered to be within the scope of the invention. In particular, the following modifications and variations fall within the scope of the invention:

- LEDs 14 may have a fixed illumination angle. In this arrangement, a collimator, or other like device, may be positioned in front of each LED 14. On choosing a setting, the collimator, or other like device, will operate to restrict or enlarge, as appropriate, the beam of light 26 generated by the LED 14 such that the circle generated by the beam of light 26 at the point of intersection with the ophthalmic lens 16 is of substantially the same size as the pupil 24 size associated with the setting. A similar collimator arrangement can be implemented in respect of the third embodiment of the invention.
- The ophthalmic camera 10, 50 and ophthalmic camera adaptor 100 may include magnification lenses. Each magnification lens is associated with at least one setting, such that, on choosing the setting, the magnification lens is positioned within the optical axis X of the monochromatic camera 12 and in-between the ophthalmic lens 16 and the camera lens 18.
- Camera 12 may be a monochromatic camera. Additionally, camera 12 may be a digital camera.
- LEDs 14, 54 can be replaced by a light focusing means and light bulb arrangement.
- Beamsplitter 58 may be replaced with a prism arrangement.
- The ophthalmic lens 16 may be replaced with any other type of lens.
- The plurality of LEDs 14 may be replaced with a single LED 14 disposed about the circumference of the camera lens 18. Alternatively, more or less LEDs 14 may be used than have been described herein.
- An alternate number of settings may be used than has been described herein. Alternatively, rather than having settings that move the LEDs 14 to predefined positions, the linear and pivotal movement of LEDs 14 may be facilitated through separate manual controls. Similarly, the illumination angle of beam of light 26 and the field of view of camera lens 18 may be facilitated through separate manual controls.
- The linear and pivotal movement of LEDs 14, the illumination angle of beam of light 26 and the field of view of camera lens 18 may be facilitated through a single manual control.
- The intensity of the LEDs 14, 54 may be controlled by means of settings representing the various pupil colours. Alternatively, the intensity of the LEDs 14, 54 may be controlled by manual adjustment across the spectrum of intensities.
- An iris structure may be used to assist in limiting the field of view of the camera lens 18. The iris may be manually or automatically controlled.
- Control unit 20 may be adapted to control the linear and pivotal movement of LEDs 14, the illumination angle of beam of light 26 and the field of view of camera lens 18 based on the determined size of the pupil 24 to be examined.
- The linear movement of the ophthalmic lens 18 as a means of focusing the image to be captured can be replaced by other focusing structures.
- The adaptor structure mentioned above can be replaced with any other structure incorporating the optical arrangement mentioned.
- The interface contact 112 may be omitted and in its place control unit 20 may be in-built into the adaptor.

It should be further appreciated by the person skilled in the art that features and modifications discussed above, not being alternatives or substitutes, can be combined to form yet other embodiments that fall within the scope of the invention described.

The invention claimed is:

1. An ophthalmic camera for taking an image of the fundus of an eye, comprising:
    a camera having a camera lens;
    at least one illumination means; and
    a second lens, the centres of the second lens and camera lens being aligned to form an alignment axis, wherein the beam of light emitted by the illumination means is able to be focused by the second lens through the pupil of the eye onto the fundus,
    the illumination means comprises a plurality of light sources, the plurality of light sources being disposed around the circumference of the camera lens, and wherein the illumination means is set to a setting representative of the pupil, the setting specifying a position of the illumination means linearly along its radial axis and pivoted about the axial plane such that the circle of light emitted by the illumination means is focused relative to the centre of the second lens.

2. An ophthalmic camera as claimed in claim 1, wherein the plurality of light sources comprises a plurality of LEDs configured to provide, in use, a light beam emitted directly towards the second lens to be focused by the second lens through the pupil onto the fundus.

3. An ophthalmic camera as claimed in claim 2, wherein the plurality of LEDs are mounted proximate to the camera lens to be movable relative thereto.

4. An ophthalmic camera for taking an image of the fundus of an eye, comprising:
a camera having a camera lens;
at least one illumination means; and
a second lens, the centres of the second lens and camera lens being aligned to form an alignment axis, wherein the beam of light emitted by the illumination means is able to be focused by the second lens through the pupil of the eye onto the fundus, the illumination means comprises a plurality of LEDs configured to provide, in use, a light beam emitted directly towards the second lens to be focused by the second lens through the pupil onto the fundus,
the plurality of LEDs are mounted proximate to the camera lens to be movable relative thereto,
the plurality of LEDs are disposed to surround the circumference of the camera lens and spaced equidistant from adjacent LEDs, and
the plurality of LEDs are set to a setting representative of the pupil, the setting specifying a position of each LED of the plurality of LEDs linearly along its radial axis and pivoted about the axial plane such that the circle of light emitted by the plurality of LEDs is focused relative to the centre of the second lens.

5. An ophthalmic camera as claimed in claim 1, further comprising control means, the control means having a plurality of settings such that, when the setting of the control means is changed, said illumination means moves linearly along its radial axis to the position specified by the new setting and pivots about the axial plane until the circle of light emitted by said illumination means is focused relative to the centre of the second lens.

6. An ophthalmic camera for taking an image of the fundus of an eye, comprising:
a camera having a camera lens;
at least one illumination means; and
a second lens, the centres of the second lens and camera lens being aligned to form an alignment axis, wherein the beam of light emitted by the illumination means is able to be focused by the second lens through the pupil of the eye onto the fundus, and
wherein the ophthalmic camera further comprises:
control means, the control means having a plurality of settings such that, when the setting of the control means is changed, said illumination means moves linearly along its radial axis to the position specified by the new setting and pivots about the axial plane until the circle of light emitted by said illumination means is focused relative to the centre of the second lens; and
automated measuring means, the automated measuring means operable to analyse a fundus being examined and change the setting of the control means to the most appropriate setting on the basis of the analysis of the pupil.

7. An ophthalmic camera for taking an image of the fundus of an eye, comprising:
a camera having a camera lens;
at least one illumination means; and
a second lens, the centres of the second lens and camera lens being aligned to form an alignment axis, wherein so that the beam of light emitted by the illumination means is able to be focused by the second lens through the pupil of the eye onto the fundus, and
wherein the ophthalmic camera further comprises a first polarizer located within the alignment axis and positioned in front of the second lens and a second polarizer attached to each illumination means such that light emitted by the illumination means passes through the second polarizer, the first polarizer being oppositely polarized to the second polarizer to thereby filter the light.

8. An ophthalmic camera as claimed in claim 1, wherein the second lens is an ophthalmic lens.

9. An ophthalmic camera as claimed in claim 1, wherein the camera has a high sensitivity to low light.

10. An ophthalmic camera as claimed in claim 8, wherein the second lens is in the range of 20 to 90 dioptres.

11. An ophthalmic camera as claimed in claim 1, wherein the second lens is an ophthalmic lens and is substantially 40 dioptres.

12. An ophthalmic camera as claimed in claim 1, including focusing means for focusing the second lens.

13. An ophthalmic camera as claimed in claim 12, wherein the focusing means is means for allowing linear movement of the second lens along the alignment axis.

14. An ophthalmic camera as claimed in claim 1, wherein the illumination angle of the illumination means is adjustable.

15. An ophthalmic camera as claimed in claim 14, including at least one collimator, each collimator associated with an illumination means operable to adjust the illumination angle of the associated illumination means.

16. An ophthalmic camera as claimed in claim 1, wherein the field of view of the camera lens is adjustable.

17. An ophthalmic camera as claimed in claim 16, including an iris, the iris operable to adjust the field of view of the camera lens.

18. An ophthalmic camera as claimed in claim 1, wherein the intensity of the light generated by the illumination means is adjustable.

19. An ophthalmic camera as claimed in claim 1, wherein the illumination means is a solid state light emitting diode.

20. An ophthalmic camera as claimed in claim 1, wherein the illumination means is a light bulb with associated appropriate focusing means.

21. An ophthalmic camera as claimed in claim 1, wherein at least one surface of at least one lens has an anti-reflective coating.

22. An adaptor for an ophthalmic camera the adaptor comprising:
optics for illuminating a subject within the optical axis of the ophthalmic camera for taking an image of the fundus of an eye, the ophthalmic camera having a body and a camera housed within the body, the camera having a camera lens;
at least one illumination means;
a second lens, the centres of the second lens and camera lens being aligned to form an alignment axis, wherein the beam of light emitted by the illumination means is able to be focused by the second lens through the pupil of the eye onto the fundus;
means for releasably engaging the body; and
an aperture extending therethrough;
wherein, when releasably engaged with the body, the aperture aligns with the optical axis such that least a portion of the optical axis of the ophthalmic camera is not obscured.

23. A method of imaging a fundus comprising the steps of:
moving an illumination means along a radial axis of a camera lens; and pivoting the illumination means such that the circle of light emitted by the illumination means can be focused relative to the centre of a second lens;
wherein the centre of the second lens is in alignment with the centre of the camera lens.

24. A method of imaging a fundus as claimed in claim 23, including the further step of:
moving the illumination means along the radial axis to a predetermined position associated with a setting of a control means when the control means is set to the associated setting.

25. A method of imaging a fundus as claimed in claim 24, including the steps of:
analysing the pupil being examined;
determining the most appropriate associated setting on the basis of the analysis of the pupil; and
changing the setting of the control means to the most appropriate associated setting.

26. A method of imaging a fundus as claimed in claim 23, including the steps of:
directing the circle of light through a first polarizer; and
taking an image of the circle of light through a second polarizer of opposite polarization to the first polarizer.

27. An ophthalmic camera as claimed in claim 1,
wherein the illumination means is pivotable so that an illumination axis of the beam of light emitted is adjustable in direction.

28. The ophthalmic camera as claimed in claim 1, wherein the illumination means is moveable relative to the alignment axis and the second lens, so that the beam of light emitted by the illumination means is able to be focused by the second lens through the pupil of the eye onto the fundus.

29. The adaptor as claimed in claim 22, wherein the illumination means is moveable relative to the alignment axis and the second lens, so that the beam of light emitted by the illumination means is able to be focused by the second lens through the pupil of the eye onto the fundus.

* * * * *